(12) United States Patent
Liu et al.

(10) Patent No.: US 11,319,565 B2
(45) Date of Patent: May 3, 2022

(54) METHOD FOR PREPARING LIPOAMINO ACIDS BASED ON DEEP EUTECTIC SOLVENTS

(71) Applicant: Jiangnan University, Wuxi (CN)

(72) Inventors: Yuanfa Liu, Wuxi (CN); Binbin Nian, Wuxi (CN); Chen Cao, Wuxi (CN); Zhaojun Zheng, Wuxi (CN); Yongjiang Xu, Wuxi (CN); Yinghong Zhai, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/139,067

(22) Filed: Dec. 31, 2020

(65) Prior Publication Data

US 2021/0130862 A1 May 6, 2021

Related U.S. Application Data

(63) Continuation of application No. PCT/CN2019/113559, filed on Oct. 28, 2019.

(30) Foreign Application Priority Data

Mar. 14, 2019 (CN) .......................... 201910193954.1
May 27, 2019 (CN) .......................... 201910447896.0

(51) Int. Cl.
*C12P 13/08* (2006.01)

(52) U.S. Cl.
CPC ........ *C12P 13/08* (2013.01); *C12Y 301/01003* (2013.01)

(58) Field of Classification Search
CPC ........ C12P 13/02; C12P 13/08; C07C 231/02; C07C 233/47; C12Y 301/01003; A23L 29/10
See application file for complete search history.

(56) References Cited

U.S. PATENT DOCUMENTS 8,247,198 B2 * 8/2012 Gorke ...................... C12N 9/00 435/129
2009/0117628 A1 5/2009 Gorke et al.

FOREIGN PATENT DOCUMENTS

| CN | 105531367 A | 4/2016 |
| CN | 108588153 A | 9/2018 |
| CN | 109776348 A | 5/2019 |
| CN | 110042130 A | 7/2019 |

OTHER PUBLICATIONS

Martins TFSM., Enzymatic development of lipoaminoacids towards nanostructured delivery systems. Master's Thesis, Universidade de Lisboa (Univ., of Lisbon), Portugal, 2018, pp. 1-97. (Year: 2018).*
Sigma-Aldrich Product Specification, 1 page, downloaded on Nov. 12, 2021 from sigma-aldrich.com. (Year: 2021).*
Tripathy et al., Synthesis, chemistry, physicochemical properties and industrial applications of amino acid surfactants: A review. C.R. Chimie, 2018, vol. 21: 112-130. (Year: 2018).*
Zhao et al., New eutectic ionic liquids for lipase activation and enzymatic preparation of biodiesel. Org. Biomol. Chem., 2011, vol. 9: 1908-1916. (Year: 2011).*
Zhang et al., Green deep eutectic solvent assisted enzymatic preparation of biodiesel from yellow horn seed oil with microwave irradiation. J. Mol. Catalysis B: Enz., 2016, vol. 123: 35-40. (Year: 2016).*
Nian. B. B. et al. "Lipase and Metal Chloride Hydrate—Natural Deep Eutectic Solvents Synergistically Catalyze Amidation Reaction via Multiple Nocovalent Bond Interactions" ACS Sustainable Chemistry and Engineering, vol. 7. Oct. 10, 2019 (Oct. 10, 2019). pp. 18174-18184.
Wada, E. et al. "Enzymatic Synthesis of N-Acyl-L-Amino Acids in a Glycerol-Water System Using Acylase I from Pig Kidney" JAOCS, vol. 79 No. 1. Dec. 31, 2002 (Dec. 31, 2002). pp. 41-46.
Bernal. C. et al. "Slective and eco-friendly synthesis of lipoaminoacid-based surfactants for food, using immobilized lipase and protease biocatalysts" Food Chemistry, vol. 239,, Jun. 20, 2017 (Jun. 20, 2017), pp. 189-195.
Zhao, H. et al. "Ionic liquids and deep eutectic solvents for biodiesel synthesis: a review" Journal of Chemical Technology and Biotechnology, vol. 88, Nov. 14, 2012 (Nov. 14, 2012),pp. 3-12.

* cited by examiner

*Primary Examiner* — Ganapathirama Raghu
(74) *Attorney, Agent, or Firm* — IPro, PLLC (57) ABSTRACT

The disclosure discloses a method for preparing a lipoamino acid compound based on deep eutectic solvents, and belongs to the field of organic synthesis. The preparation method of the disclosure uses a fatty acid and an amino acid as substrates, uses a deep eutectic solvent as a medium, and directly and efficiently prepares a single-chain lipoamino acid surfactant under the catalysis of lipase CALB. Alternatively, Amano lipase M is used as a catalyst to efficiently catalyze the reaction of an amino acid containing a plurality of amino groups with a fatty acid to prepare a Gemini amino acid. The method of the disclosure does not need to undergo protection and deprotection of the amino acid, and does not involve commonly used fatty acid chlorides. Compared with the traditional chemical synthesis methods, the disclosure has the advantages of greenness, safety, high selectivity, high yield, etc., and has very important potential application value.

14 Claims, 8 Drawing Sheets

METHOD FOR PREPARING LIPOAMINO ACIDS BASED ON DEEP EUTECTIC SOLVENTS

TECHNICAL FIELD

The disclosure herein relates to a method for preparing lipoamino acids based on deep eutectic solvents, and belongs to the field of organic synthesis.

BACKGROUND

Surfactants are often used as emulsifiers, thickeners, defoamers and many other agents in the food field due to their unique properties. They are called "industrial monosodium glutamate" and are in great demand. In recent years, the research on lipoamino acid surfactants has become a hot spot. Traditional lipoamino acid surfactants are mostly quaternary ammonium salts. Although they have good surface activity and antibacterial properties, they also have a certain degree of cytotoxicity, which limits their large-scale application in the food field. Compared with the traditional surfactants, lipoamino acid surfactants have higher safety and have better application prospects in the food field.

At present, most research on the synthesis of the lipoamino acid surfactants focuses on chemical methods, which cause great pollution to the environment. An enzymatic synthesis process mostly uses an organic solvent as the reaction system, which is not only unfavorable to the environment, but also easily leads to enzyme denaturation and inactivation. The current preparation methods include using lipase Novozyme435 as a catalyst to synthesize a glyceryl-arginine surfactant in a solvent-free system, and the synthesis yield is only 15%. Therefore, how to find a suitable green solvent has become a major problem that limits the synthesis and application of the lipoamino acid surfactants.

Natural deep eutectic solvents have been widely used in esterification reactions. Unlike esterification reactions, the reaction of fatty acids and amino acids usually produces quaternary ammonium salts instead of lipoamino acids. In order to improve the yield of lipoamino acids, a two-step method is currently used, that is, firstly activating the fatty acid and then carrying out a nucleophilic reaction of the amino acid. Therefore, the problems of many by-products, low product synthesis efficiency, etc. are caused.

In addition, as a new generation of lipoamino acids, Gemini lipoamino acids consist of two hydrophilic or two hydrophobic groups and can be considered as a dimer of lipoamino acids. It is currently reported that the CMC value of the Gemini lipoamino acids can be one or even several orders of magnitude lower than that of single-chain surfactants. It is also reported that a series of new L-lysine-based Gemini surfactants have been synthesized, and compared with traditional lipoamino acids, they have better antibacterial activity in a broad spectrum of gram-positive and gram-negative bacteria. Although the Gemini lipoamino acids have many advantages mentioned-above, they have not been applied industrially, because currently the Gemini lipoamino acids can only be prepared by complex multi-step organic synthesis. The existing synthesis of the Gemini lipoamino acids is mostly accomplished by the Schotten-Baumann reaction. The reaction uses fatty acid chlorides instead of fatty acids as raw materials. Although the product yield is improved to a certain extent, there are still great safety hazards and environmental problems.

In order to alleviate the pollution and safety issues in the production of the Gemini lipoamino acids, enzymatic synthesis has been gradually emphasized. However, the current enzymatic synthesis still has a series of problems that are difficult to solve, mainly focusing on the difficulty of finding a solvent that has good substrate solubility while maintaining high enzyme activity. These problems all lead to a low yield of the Gemini lipoamino acids prepared by enzymatic synthesis.

SUMMARY

The disclosure discloses a method for preparing a lipoamino acid compound, including:

directly preparing the lipoamino acid compound from a fatty acid and an amino acid under the action of a catalyst with a deep eutectic solvent as a medium.

In an embodiment of the disclosure, a molar ratio of the fatty acid to the amino acid is 1:1 to 2:1.

In an embodiment of the disclosure, the amino acid includes glycine, lysine, arginine, and alanine.

In an embodiment of the disclosure, the fatty acid is a C2-C20 fatty acid.

In an embodiment of the disclosure, the fatty acid includes lauric acid and palmitic acid.

In an embodiment of the disclosure, the catalyst includes lipase CALB (lipase B from *Candida antarctica*, specification 5,000 LU/g).

In an embodiment of the disclosure, according to the characteristics of the amidation reaction and the solubility of amino acids and fatty acids, the commonly used deep eutectic solvents are screened, and the deep eutectic solvent includes any one of betaine-glycerin, betaine-xylitol, choline chloride-glycerin, and choline chloride-xylitol.

In an embodiment of the disclosure, the deep eutectic solvent is prepared from a hydrogen bond donor and a hydrogen bond acceptor in a certain stoichiometric ratio by rotary evaporation at 60-100° C.

In an embodiment of the disclosure, a stoichiometric ratio of the hydrogen bond donor to the hydrogen bond acceptor is 2:1 to 1:2.

In an embodiment of the disclosure, the method is carried out at 40-60° C., a pH value of 7.0-8.0, and a stirring speed of 200-300 rpm.

In an example of the disclosure, the amount of water is 50%-100% (V/V) of the reaction system.

The disclosure further discloses a method for preparing a surfactant. The method includes preparing a lipoamino acid compound in advance, and then preparing the surfactant. The preparation method of the lipoamino acid compound is the above method.

The disclosure further discloses an emulsifier. The method includes preparing a lipoamino acid compound in advance, and then preparing the emulsifier. The preparation method of the lipoamino acid compound is the above method.

The disclosure further discloses a thickener. The method includes preparing a lipoamino acid compound in advance, and then preparing the thickener. The preparation method of the lipoamino acid compound is the above method.

The disclosure further discloses a defoamer. The method includes preparing a lipoamino acid compound in advance, and then preparing the defoamer. The preparation method of the lipoamino acid compound is the above method.

The disclosure further discloses a method for preparing a Gemini lipoamino acid, including in a deep eutectic solvent, Amano lipase M is used as a catalyst, an amino acid and a fatty acid react to obtain a Gemini amino acid; a hydrogen bond donor in the deep eutectic solvent includes oleic acid and/or linoleic acid, and a hydrogen bond acceptor is choline chloride; and the number of amino groups in the amino acid is not less than 2.

In an embodiment of the disclosure, the amino acid includes lysine, cystine, and arginine.

In an embodiment of the disclosure, the fatty acid is a C2-C20 fatty acid.

In an embodiment of the disclosure, the fatty acid includes lauric acid and palmitic acid.

In an embodiment of the disclosure, the deep eutectic solvent is preferably choline chloride-oleic acid.

In an embodiment of the disclosure, the deep eutectic solvent is prepared from the hydrogen bond donor and the hydrogen bond acceptor in a certain stoichiometric ratio by rotary evaporation at 60-100° C.

In an embodiment of the disclosure, a stoichiometric ratio of the hydrogen bond donor to the hydrogen bond acceptor in the deep eutectic solvent is 2:1 to 1:2.

In an embodiment of the disclosure, the temperature of the reaction is 40-80° C.

In an embodiment of the disclosure, the temperature of the reaction is preferably 60° C.

In an embodiment of the disclosure, the addition amount of the Amano lipase M is 50-100 mg per mole of amino acid.

In an embodiment of the disclosure, the addition amount of the Amano lipase M is preferably 60-75 mg per mole of amino acid.

In an embodiment of the disclosure, the Amano lipase M comes from Mucor (MJL), CAS NO: 9001-62-1.

In an embodiment of the disclosure, a molar ratio of the fatty acid to the amino acid is 2.5:1 to 1:1.

In an example of the disclosure, the product obtained from the reaction undergoes the following purification process: extraction with ethyl acetate and water, and recrystallization with methanol to obtain a pure product.

In an example of the disclosure, each 20 mL of reaction system uses 50-100 mL of ethyl acetate and 250-500 mL of water for extraction.

The disclosure further discloses a method for preparing a food emulsifier by using the above method.

Compared with the prior art, the disclosure has the following beneficial effects:

(1) The disclosure uses the green and safe natural deep eutectic solvent instead of the traditional organic reagent as the reaction medium, without water as an auxiliary mixed solvent. Not only is the pollution to the environment greatly reduced, but also the current situation of low substrate solubility and poor lipase activity in the traditional organic solvent enzymatic synthesis process of lipoamino acids is greatly changed because of good substrate solubility of the natural deep eutectic solvent and the ability to better maintain the stability and activity of the enzyme. The reaction yield is significantly higher than that of enzymatic synthesis of lipoamino acids by other reported methods. In addition, the current enzymatic synthesis using the natural deep eutectic solvent is mostly characterized by a substrate conversion rate, which cannot indicate the level of product yield, and basically does not involve the product purification process. The disclosure adopts a simple and efficient water washing-methanol recrystallization method to obtain the product with higher purity, and greatly simplifies the purification process of enzymatic synthesis of lipoamino acids.

(2) Using the natural deep eutectic solvent instead of the traditional organic solvents as the reaction medium not only solves the problem of substrate solubility, but also maintains higher enzyme activity. In addition, the disclosure reports for the first time that the natural deep eutectic solvent has a synergistic catalytic effect with enzymes, and on this basis, a Gemini lipoamino acid food emulsifier is successfully synthesized with a higher product yield (the yield can reach 59.6%), breaking the bottleneck of domestic synthesis of the Gemini lipoamino acid. In addition, the disclosure further designs a simplified product purification process which uses ethyl acetate and water for extraction and uses methanol recrystallization to obtain a product with higher purity. In order to further reduce the production cost, the disclosure further recycles the natural deep eutectic solvent through simple treatment. After 10 cycles, the synthesis yield still can reach 52.4%, maintaining 88.48% of the initial effect, so the disclosure has excellent effects and greatly reduces the production costs.

DETAILED DESCRIPTION

Figure 1:
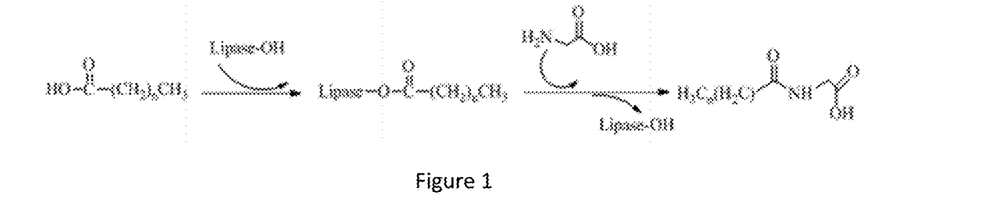
FIG. 1 is a synthetic route diagram of lipoamino acids.

The main idea of the disclosure is as follows:

(1) A new idea is provided for enzymatic synthesis of lipoamino acids, that is, a series of enzyme-friendly solvents with good substrate solubility are used. The disclosure first inspects the solubility of the natural deep eutectic solvent to the substrate, secondly inspects the influence of the solvent on the activity and stability of the enzymes and the mechanisms, and finally, carries out synthesis experiments of the lipoamino acids. A synthesis process includes two steps: 1) combination of lipase with a fatty acid to complete activation of the fatty acid; and 2) nucleophilic attack of the amino group of an amino acid on the activated fatty acid intermediate to form amide. The specific steps are shown in FIG. 1.

(2) A new idea is provided for enzymatic synthesis of Gemini lipoamino acids, that is, a series of green solvents that have a synergistic catalytic effect with enzymes are used as the reaction medium.

The disclosure first inspects the synthesis method of the Gemini lipoamino acids in traditional organic solvents, and secondly inspects the self-designed synthesis method of lipoamino acids in the natural deep eutectic solvent. The inspection content includes: enzyme screening, solvent screening, reaction condition optimization, solvent recycling, and product purification.

The disclosure will be further described in detail below in conjunction with specific examples.

Yield of Gemini lipoamino acid=Actual value of Gemini lipoamino acid/Theoretical value of Gemini lipoamino acid.

The CMC value is determined by a conductivity method: The relationship between the conductivity of an ionic surfactant aqueous solution and the concentration is used to draw a $\wedge_m$-$C^{1/2}$ curve, and the CMC value is derived from the turning point of the curve.

$\wedge m = K/C$. The unit of $\wedge m$ is $S \cdot m^2/mol$, and the unit of C is mol/L.

For a strong electrolyte, if the temperature is constant, the molar conductivity $\wedge m$ of the strong electrolyte solution has a linear relationship with the concentration of the solution $c^{1/2}$ in an extremely low concentration range. For a colloidal electrolyte, the conductivity and molar conductivity of a dilute solution change in the same way as the strong electrolyte. However, with the formation of micelles in the solution, the electrical conductivity and molar conductivity change significantly, which is the basis for determining the CMC.

Example 1 Preparation of Single-Chain Lauroyl Glycine 25 mM lauric acid and 25 mM glycine were respectively weighed and placed in a 25 ml reaction flask, and 10 ml of natural deep eutectic solvent (choline chloride-glycerin in a ratio of 1:2) and 12.5 mg of lipase CALB (5,000 LU/g) were added into the reaction flask. Then the reaction flask was sealed and placed on a thermostatic water bath shaker for a continuous reaction at 60° C. and 200 rpm for 48 h.

After the reaction, the reaction flask was taken out. A large amount of water was added and shaking was carried out vigorously. Then centrifugation was carried out at 10,000 rpm for 10 min. After centrifugation, clear liquid was removed. Then vacuum suction filtration was carried out to obtain a white solid crude product. Methanol was added to the white solid crude product, and the crude product was recrystallized twice to obtain a pure product single-chain lauroyl glycine with a purity of 98%. The yield of the pure product was 50.49%.

Figure 6:
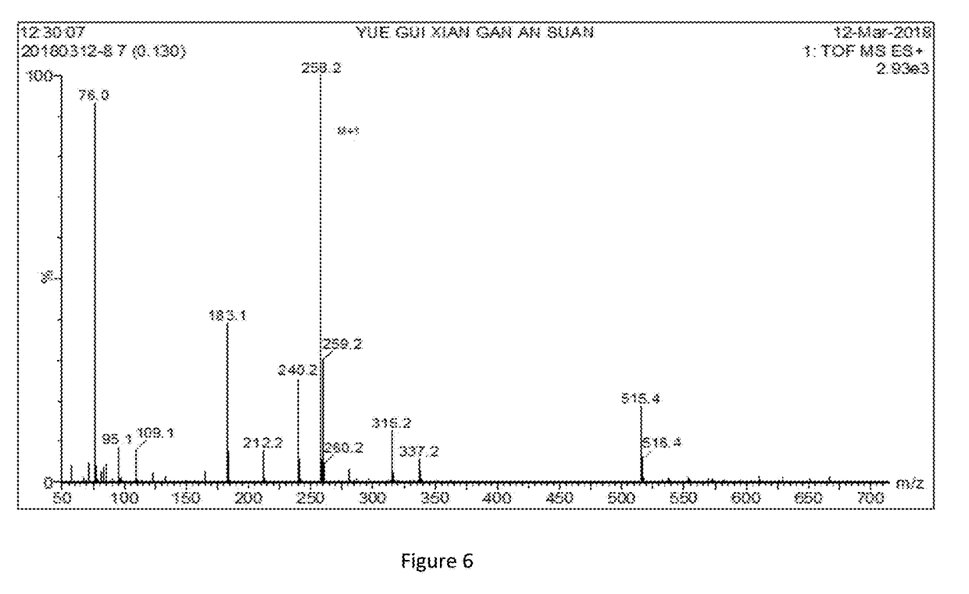
FIG. 6 is a mass spectrum of the product.
Figure 7:
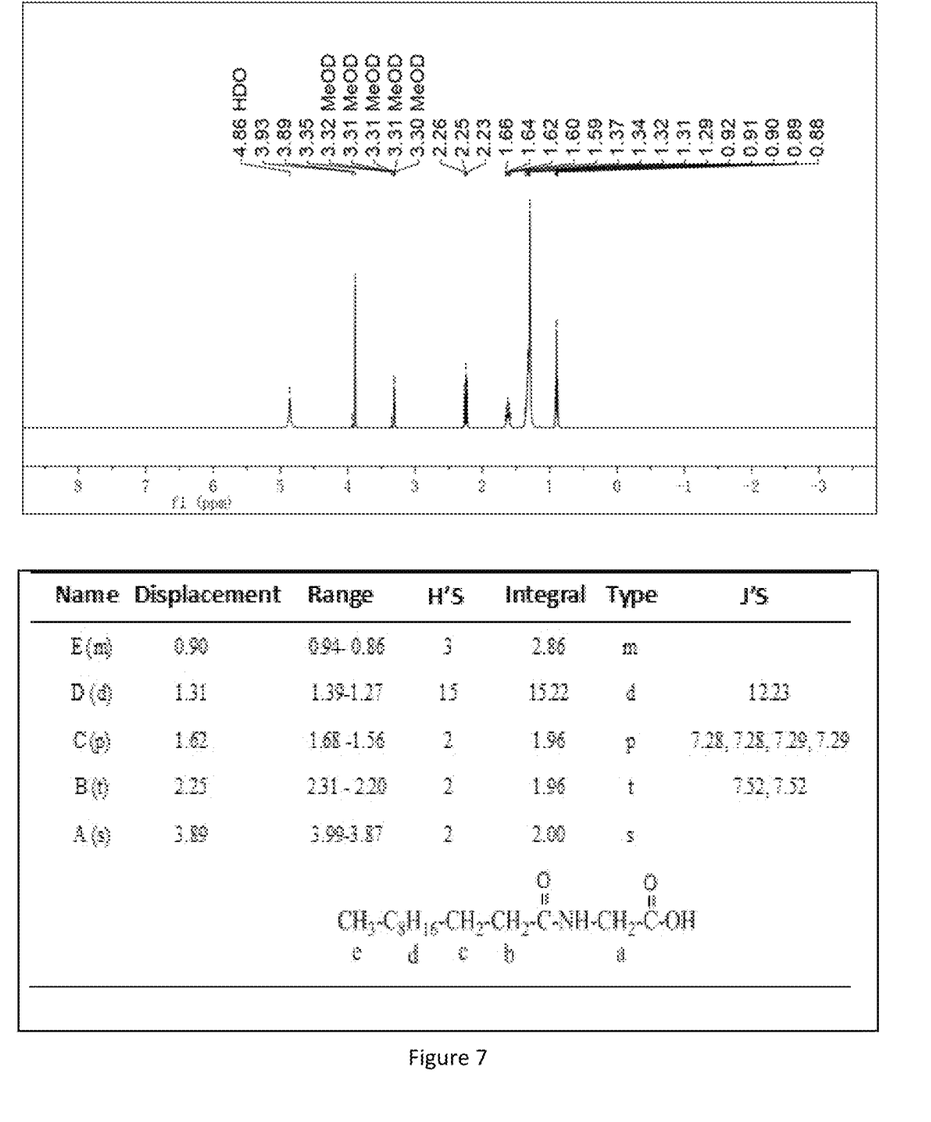
FIG. 7 is a hydrogen nuclear magnetic resonance spectrum and its corresponding data chart.

It can be seen from the mass spectrum in FIG. 6 that dipeptide, a common by-product in the synthesis process of lipoamino acids, does not appear in the pure product. This shows that the preparation method of the present example has a higher product yield and few by-products.

The CMC value of the product was measured by the conductivity method. The CMC value of the lauroyl glycine is 0.0044 mol/L, which is significantly lower than the CMC value of the current commonly-used surfactant Tween sodium dodecyl sulfonate (0.009 mol/L), so the lauroyl glycine is a surfactant with better performance.

Example 2 Preparation of Single-Chain Lauroyl Glycine 25 mM lauric acid and 25 mM glycine were respectively weighed and placed in a 25 ml reaction flask, and 10 ml of natural deep eutectic solvent (betaine-glycerin in a ratio of 1:2) and 12.5 mg of lipase CALB (5,000 LU/g) were added into the reaction flask. Then the reaction flask was sealed and placed on a thermostatic water bath shaker for a continuous reaction at 60° C. and 200 rpm for 48 h.

After the reaction, the reaction flask was taken out. A large amount of water was added and shaking was carried out vigorously. Then centrifugation was carried out at 10,000 rpm for 10 min. After centrifugation, clear liquid was removed. Then vacuum suction filtration was carried out to obtain a white solid crude product. Methanol was added to the white solid crude product, and the crude product was recrystallized twice to obtain a pure product with a purity of 98%. The final yield of the pure product was 43.98%.

Example 3 Preparation of Single-Chain Lauroyl Glycine 25 mM lauric acid and 25 mM glycine were respectively weighed and placed in a 25 ml reaction flask, and 10 ml of natural deep eutectic solvent (betaine-xylitol in a ratio of 1:2) and 12.5 mg of lipase CALB (5,000 LU/g) were added into the reaction flask. Then the reaction flask was sealed and placed on a thermostatic water bath shaker for a continuous reaction at 60° C. and 200 rpm for 48 h.

After the reaction, the reaction flask was taken out. A large amount of water was added and shaking was carried out vigorously. Then centrifugation was carried out at 10,000 rpm for 10 min. After centrifugation, clear liquid was removed. Then vacuum suction filtration was carried out to obtain a white solid crude product. Methanol was added to the white solid crude product, and the crude product was recrystallized twice to obtain a pure product with a purity of 98%. The final yield of the pure product was 38.97%.

Example 4 Preparation of Single-Chain Lauroyl Glycine 25 mM lauric acid and 25 mM glycine were respectively weighed and placed in a 25 ml reaction flask, and 10 ml of natural deep eutectic solvent (choline chloride-xylitol in a ratio of 1:2) and 12.5 mg of lipase CALB (5,000 LU/g) were added into the reaction flask. Then the reaction flask was sealed and placed on a thermostatic water bath shaker for a continuous reaction at 60° C. and 200 rpm for 48 h.

After the reaction, the reaction flask was taken out. A large amount of water was added and shaking was carried out vigorously. Then centrifugation was carried out at 10,000 rpm for 10 min. After centrifugation, clear liquid was removed. Then vacuum suction filtration was carried out to obtain a white solid crude product. Methanol was added to the white solid crude product, and the crude product was recrystallized twice to obtain a pure product with a purity of 98%. The final yield of the pure product was 41.40%.

Example 5 Inspection of Influence of Deep Eutectic Solvent on Reaction Substrate 10 g of natural deep eutectic solvent (C-Gly) was accurately weighed and placed in a thermostatic shaking water bath at 60° C. After the temperature was constant, 10 mg of lauric acid was weighed and added thereto, and the mixture was shaken at 200 rpm for 30 min. Then a drop was taken out by a capillary and detected under a polarizing microscope. If polarized light does not appear, the dissolution is complete, and then 10 mg of lauric acid is added again until the dissolution is no longer continued (polarized light appears). The final substrate solubility was calculated according to the following formula:

$$S = m_t \times 10/1000 \qquad (1).$$

Herein, S is the solubility and $m_t$ is the total addition amount of substrate. The final lauric acid solubility is 24.98 (g/100 g).

Lauric acid is slightly soluble in commonly used enzyme-friendly solvent acetone (0.01-0.1 g/100 g), and has a solubility of 0 in water.

Glycine has a solubility of 22.78 (g/100 g) in a deep eutectic solvent and a solubility of 25 g/100 g in water, and is almost insoluble in acetone.

Figure 2:
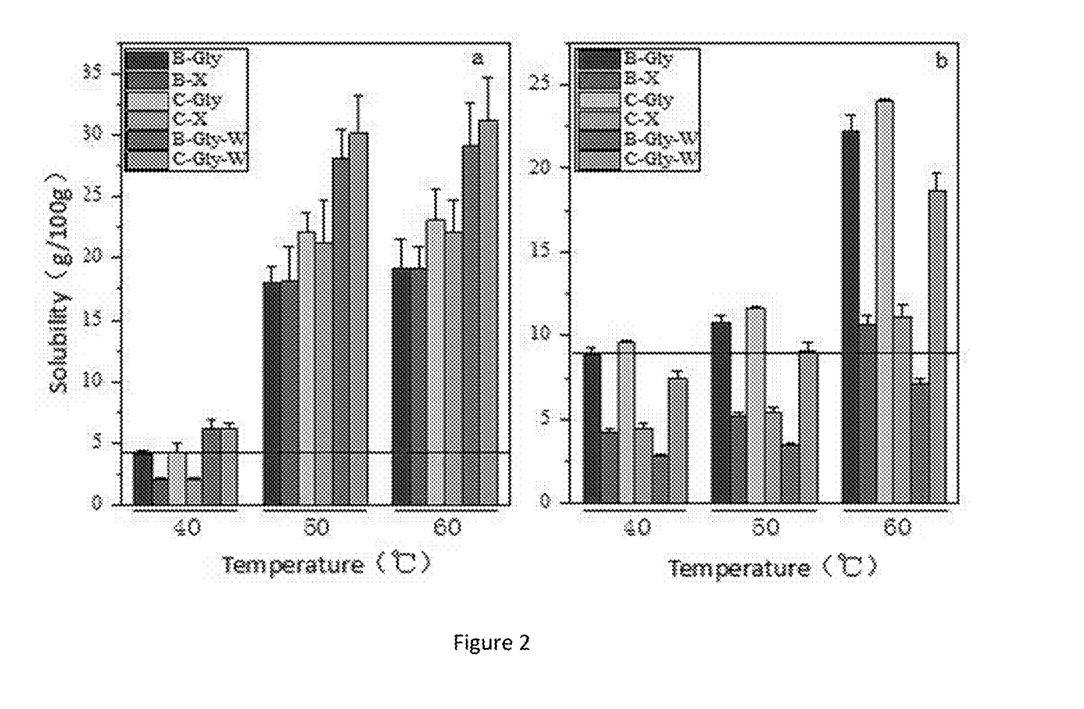
FIG. 2 shows the solubility of glycine (a) and lauric acid (b) in different natural deep eutectic solvents, and the solvents from left to right at each temperature are respectively betaine-glycerin (B-Gly), betaine-xylitol (B-X), choline chloride-glycerin (C-Gly), choline chloride-xylitol (C-X), betaine-glycerin-water (B-Gly-W), and choline chloride-glycerin-water (C-Gly-W).

It can be seen from FIG. 2 that different deep eutectic solvents have different influences on the solubility of the two substrates. Among them, C-Gly-W has the best solubility and good substrate universality.

Example 6 Inspection of Influence of Different Deep Eutectic Solvents on Lipase Catalysts Lipase activity and thermal stability were measured by pNPP assay: 10 μL of enzyme solution was added to 3990 μL of NADES (a PBS buffer, pH 8.0, as a control), and reacted at 60° C. (the optimum temperature for CALB) and 200 rpm for 120 min, 240 min and 360 min. 10 μL of reaction solution was taken out immediately and added to 80 μL of PBS buffer (50 mM, pH 8.0) and 10 μL of pNPP solution. The mixture was reacted at 60° C. and 200 rpm for 5 min, and 100 μL of ethanol (95%) was added to immediately terminate the reaction. The absorbance was measured at 405 nm with a Spectramax 190 microplate reader (Molecular Devices, German). The enzyme activity and thermal stability were calculated based on pNP.

Figure 3:
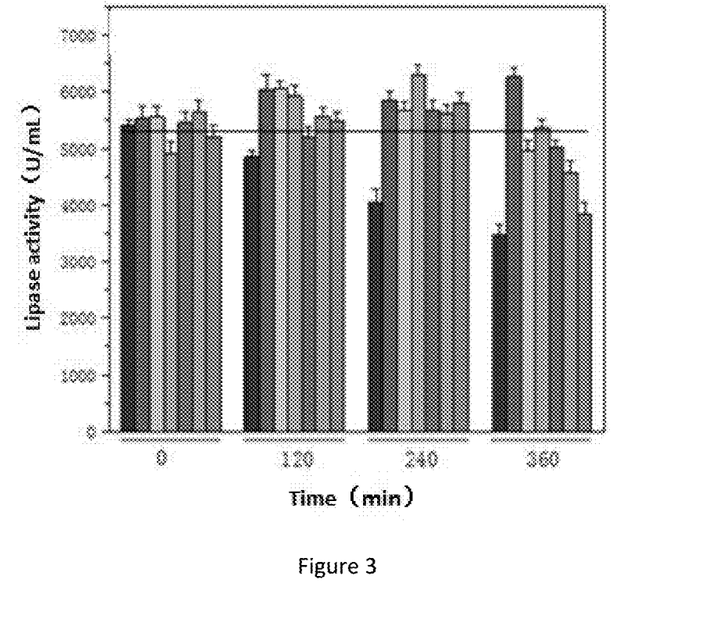
FIG. 3 shows the activity of lipase in different natural deep eutectic solvents, and the solvents from left to right at each time are respectively Tris-buffer (50 mM, pH 8.0)(as a control), betaine-glycerin (B-Gly), betaine-xylitol (B-X), choline chloride-glycerin (C-Gly), choline chloride-xylitol (C-X), betaine-glycerin-water (B-Gly-W), and choline chloride-glycerin-water (C-Gly-W).

In combination with FIG. 3, the lipase CALB can still maintain high activity after treated in NADES at 60° C. for 360 min, reaching 6,400 U/mL. The balance between structural rigidity and flexibility is the basis for high stability and activity of lipase. NADES can interact with enzymes to increase its structural rigidity, thereby improving the stability of the enzymes. In addition, what is unexpected is that, as shown in FIG. 3, in the four NADES groups without water, the lipase still maintains high activity after 360 min. In systems with the participation of water, the enzyme activity is gradually inhibited. The inventor believes that it may be because the surface of the enzymes can be bonded with NADES, such as glycerin and xylitol. These small organic molecules can form a complex hydrogen bonded network with the enzymes.

Figure 4:
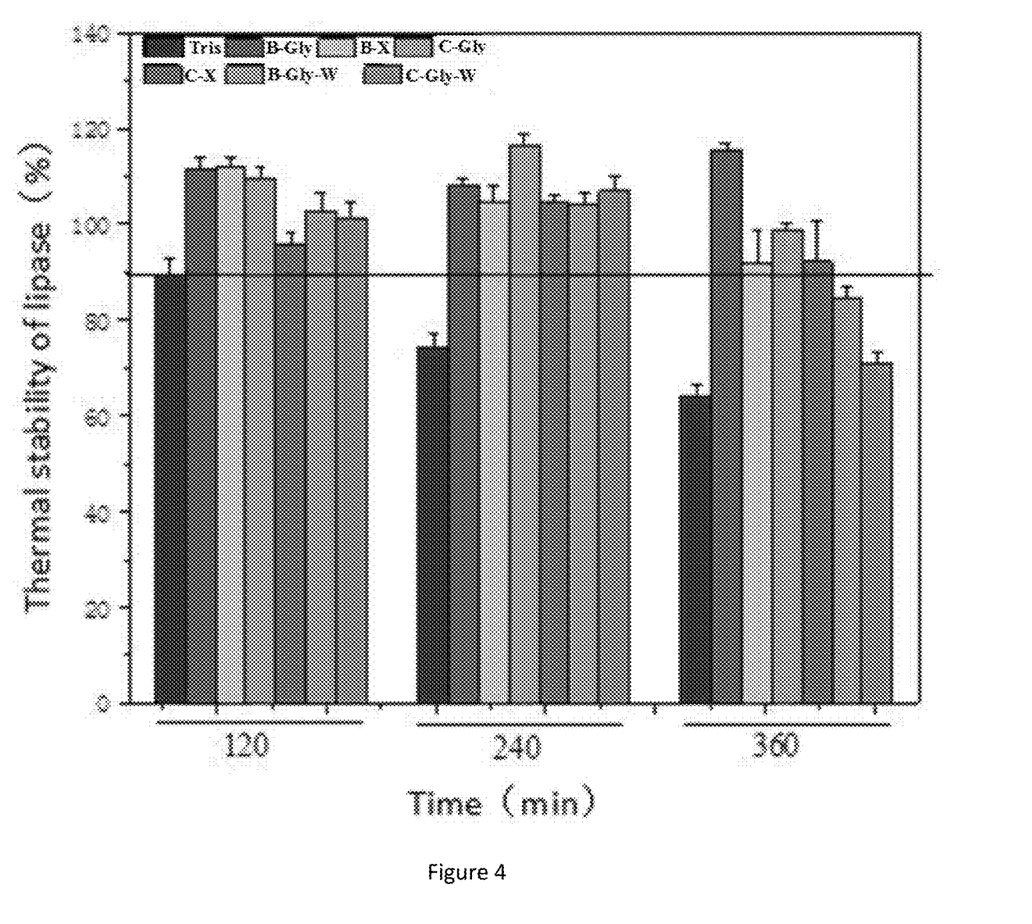
FIG. 4 shows the thermal stability of lipase in different natural deep eutectic solvents, and the solvents from left to right at each time are respectively tris-buffer (Tris), betaine-glycerin (B-Gly), betaine-xylitol (B-X), choline chloride-glycerin (C-Gly), choline chloride-xylitol (C-X), betaine-glycerin-water (B-Gly-W), and choline chloride-glycerin-water (C-Gly-W).
Figure 5:
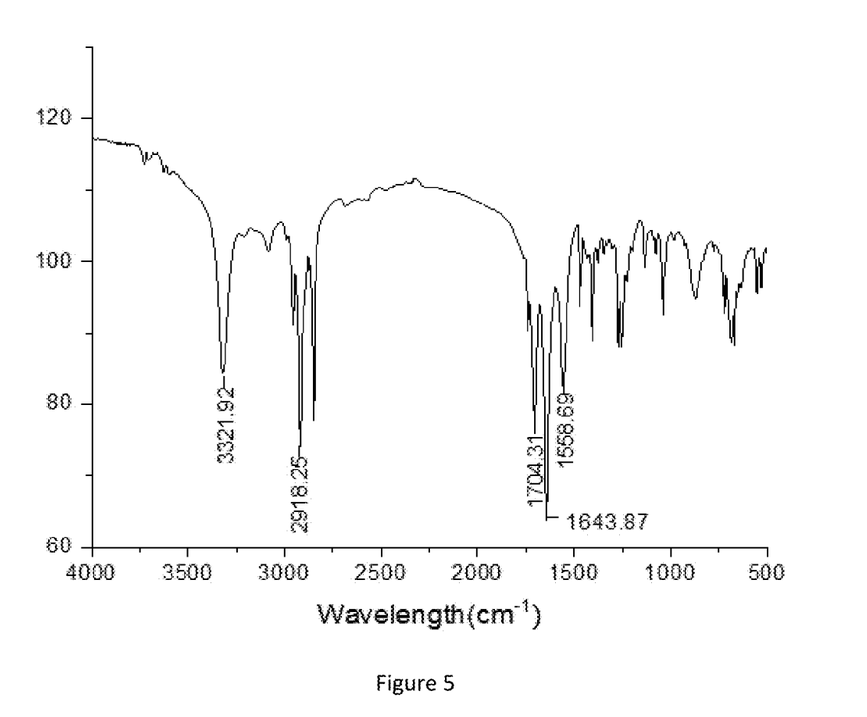
FIG. 5 is an infrared spectrum of a product.

As shown in FIG. 4, the presence of water weakens the interaction between the NADES and enzymes, and reduces the structural rigidity and the ability to resist external interference of the enzymes, resulting in a decrease in the thermal stability of lipase, which is consistent with the consequence of the enzyme activity.

Comparative Example 1

With reference to Example 1, the deep eutectic solvent was replaced with acetone, other conditions were unchanged, and the product yield was basically negligible.

Example 7 Preparation of Gemini Lauroyl Amino Acid 2.5 mmol of lauric acid, 1 mmol of L-lysine and 60 mg of Amano lipase M were taken and added to 20 mL of choline chloride-oleic acid (in a ratio of 1:2), and reacted at 500 rpm and 60° C. for 72 h. 200 mL of ultrapure water was added to the reacted mixture for dilution, and the mixture was subjected to vortex shaking for 1 min. The diluted reaction solution was centrifuged at 10,000 rpm for 20 min, precipitate was reserved, and at the same time, the water phase was collected for solvent recovery. The precipitate was diluted with 25 ml of ethyl acetate, and the fatty acid was neutralized with 20 ml of saturated sodium bicarbonate solution. The mixture was centrifuged at 10,000 rpm for 20 min and subjected to vacuum drying at 313 K for 24 h. The dried product was added to 5 ml of methanol, and the mixture was subjected to vortex for 1 min and centrifuged at 10,000 rpm for 20 min. The system stratified, and the upper layer (methanol and single-chain lipoamino acids) was removed to obtain a Gemini lipoamino acid product. The product purity was 98%, and the yield was 59.6%. In existing reports, a deep eutectic solvent (choline chloride-glycerin), combined with CALB lipase, was used to synthesize N,N-dilauroyl lysine, and the yield was 26.3%, less than half the effect of the present example.

Figure 8:
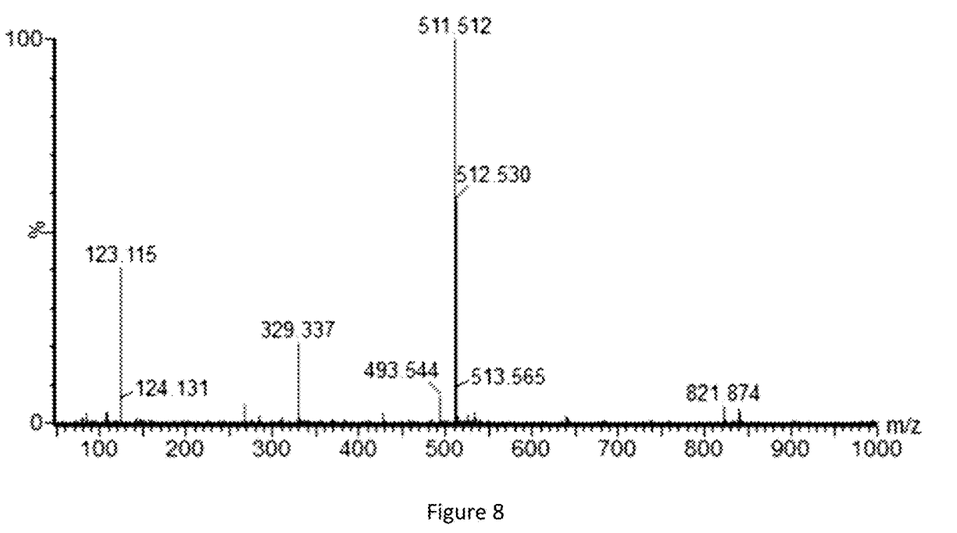
FIG. 8 is a mass spectrum of Gemini lauroyl lysine (GLL).
Figure 9:
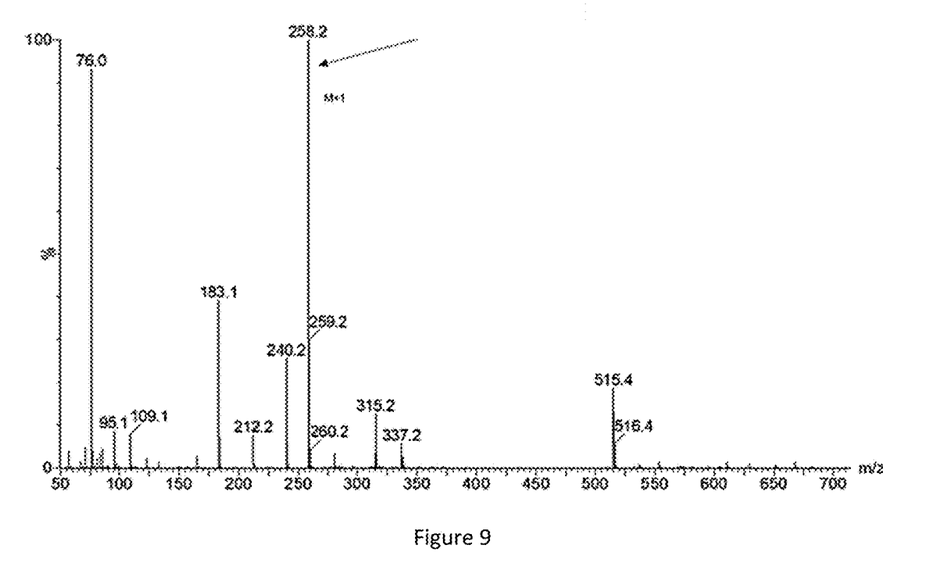
FIG. 9 is a mass spectrum of single-chain lauroyl glycine (LAA).
Figure 10:
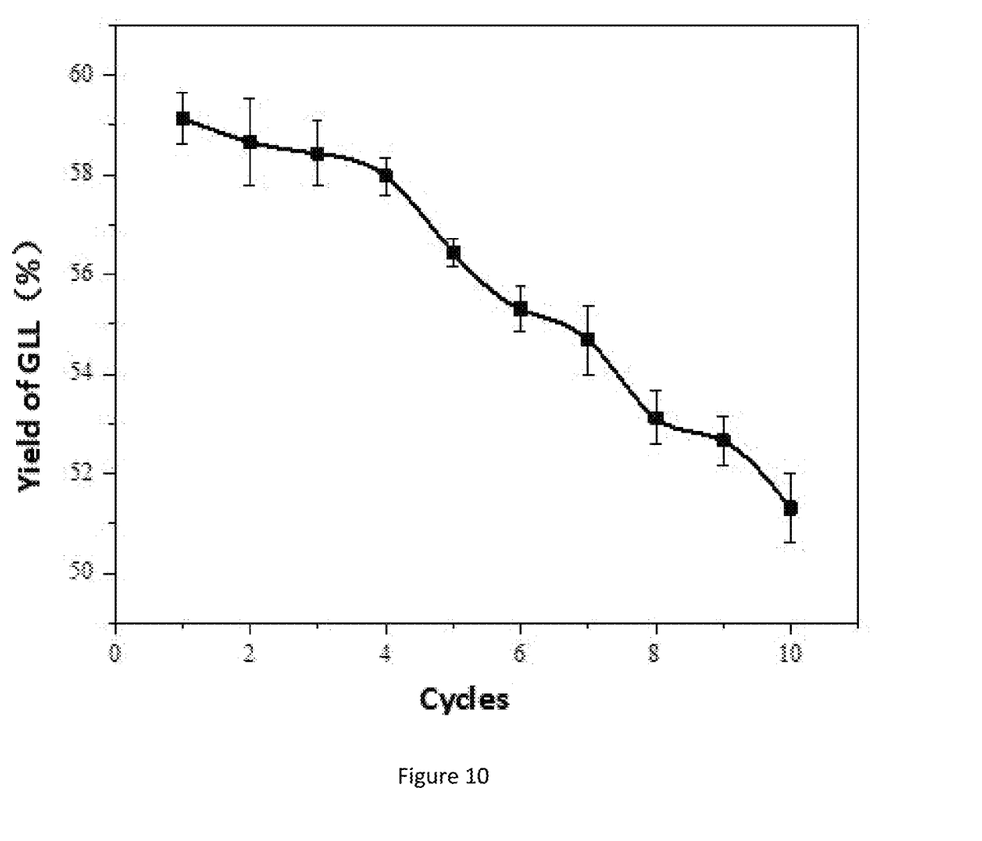
FIG. 10 shows the recycling efficiency of the deep eutectic solvent.

It can be seen from the mass spectrum in FIG. 8 that Gemini lauroyl glycine consisting of two hydrophilic or two hydrophobic groups, that is, a dimer of lipoamino acid, was prepared in the present example.

The CMC values of several products were measured by the conductivity method. The CMC of the Gemini lauroyl amino acid is 0.0044 mol/L, which is significantly lower than that of the current commonly-used surfactant Tween sodium dodecyl sulfonate (0.009 mol/L), so the Gemini lauroyl amino acid is a surfactant with better performance.

Example 8 Influence of Different Deep Eutectic Solvents on Preparation of Gemini Lipoamino Acids With reference to Example 7, the solvents were replaced with solvents shown in Table 1, other conditions were unchanged, and reactions were carried out to prepare the Gemini lipoamino acids. The results are as shown in Table 1.

TABLE 1

Results of preparation of Gemini lipoamino acids with different deep eutectic solvents

| Solvent | Yield of Gemini lipoamino acid (%) |
|---|---|
| Choline chloride-linoleic acid | 29.3 |
| Betaine-oleic acid | 22.1 |
| Choline chloride-glycerin | 18.6 |
| DMSO | NR |
| Acetone | NR |
| [C4mim]Cl | NR |

N.R. means that no product is obtained.

Example 9 Influence of Different Enzymes on Preparation of Gemini Lipoamino Acids With reference to Example 7, the enzyme catalysts were replaced with enzymes shown in Table 2, other conditions were unchanged, and reactions were carried out to prepare the Gemini lipoamino acids. The results are as shown in Table 2.

TABLE 2

Results of preparation of Gemini lipoamino acids with different enzymes

| Enzyme catalyst | Yield of Gemini lipoamino acid (%) |
|---|---|
| DA | 8.9 |
| PPL | 14.6 |
| CALB | 19.1 |
| BSAP | 6.7 |

DA is D-amino-acylase from *Escherichia coli*.
PPL is lipase from porcine pancreas.
CALB is lipase B from *Candida Antarctica*.
BSAP is alkali protease from *Bacillus subtilis*.

Example 10 Optimization of Reaction Condition Parameters

With reference to Example 7, the substrate molar ratio, reaction time, reaction temperature, addition amount of enzyme and other indicators were optimized by a single factor experimental method respectively. Table 3 shows the specific results of production of Gemini lipoamino acids.

TABLE 3

Optimization results of reaction condition parameters

| Molar ratio of lauric acid to lysine | Reaction time (h) | Addition amount of enzyme (g) | Reaction temperature (° C.) | Yield (%) |
|---|---|---|---|---|
| 2:1 | 72 | 60 | 60 | 44.3 |
| 2:1 | 72 | 60 | 80 | 45.6 |
| 2:1 | 72 | 60 | 40 | 41.3 |
| 2:1 | 72 | 60 | 60 | 50.4 |
| 2:1 | 72 | 75 | 60 | 57.6 |
| 2:1 | 72 | 50 | 60 | 51.4 |
| 2:1 | 72 | 30 | 60 | 30.3 |
| 2:1 | 96 | 60 | 60 | 48.0 |
| 2.5:1 | 72 | 60 | 60 | 59.6 |
| 1:1 | 72 | 60 | 60 | 43.9 |
| 1:2 | 72 | 60 | 60 | 28.8 |

The results show that in the reaction process, the addition amount of enzyme and the reaction temperature were the two most critical factors. At 60° C., an addition amount of enzyme of 60 mg matching the system obtained a better reaction effect.

Example 11 Inspection of Recovery Efficiency of Deep Eutectic Solvent After Reaction The water phase collected in the post-reaction treatment process was used to recover the natural deep eutectic solvent: 10 mass equivalents of ethyl acetate was added to the mixture, and the mixture was subjected to vortex for 1 min and then transferred to a separatory funnel. The organic phase was discarded while the water phase was collected. Excess water and ethyl acetate were removed by vacuum drying at 333 K for 48 h, and then the deep eutectic solvent was recovered.

The recovered deep eutectic solvent was used in the synthesis of lauroyl lysine to test the performance of the deep eutectic solvent. For specific reaction conditions, reference may be made to Example 1. After the solvent was subjected to 10 cycles, the synthesis yield of the Gemini lipoamino acids was reduced from 59.6% to 52.4%, and still can maintain 88.48% of the initial effect.

The above examples are only to illustrate the technical concept and characteristics of the disclosure. The purpose is to enable those skilled in the art to understand the content of the disclosure and implement them accordingly, and cannot limit the protection scope of the disclosure. All equivalent changes or modifications made according to the spirit of the disclosure should be covered by the protection scope of the disclosure.

What is claimed is:

1. A method for preparing a Gemini lipoamino acid compound, comprising:
   preparing the Gemini lipoamino acid compound from a fatty acid and an amino acid under action of a catalyst with a deep eutectic solvent as a medium,
   wherein the amino acid is any one of glycine, lysine, cysteine, arginine, and alanine,
   wherein the deep eutectic solvent comprises any one of betaine-glycerin, betaine-xylitol, choline chloride-glycerin, and choline chloride-xylitol,
   wherein the catalyst comprises lipase *Candida antarctica* lipase B (CALB),
   wherein the fatty acid is lauric acid or palmitic acid, and
   wherein a temperature of the reaction is 40° C. to 80° C.

2. The method according to claim 1, wherein a molar ratio of the fatty acid to the amino acid is 1:1 to 2:1.

3. The method according to claim 1, wherein a volume ratio of a hydrogen bond donor to a hydrogen bond acceptor of the deep eutectic solvent is 2:1 to 1:2.

4. The method according to claim 1, wherein in the deep eutectic solvent, lipase is used as a catalyst to catalyze a reaction of the amino acid and the fatty acid to obtain a Gemini amino acid; a hydrogen bond donor in the deep eutectic solvent comprises oleic acid and/or linoleic acid, and a hydrogen bond acceptor is choline chloride; and the number of amino groups in the amino acid is not less than 2.

5. The method according to claim 4, wherein an addition amount of the lipase is 50 to 100 mg per mole of amino acid.

6. The method according to claim 4, wherein the deep eutectic solvent consists of choline chloride and oleic acid.

7. The method according to claim 4, wherein a stoichiometric ratio of the hydrogen bond donor to the hydrogen bond acceptor in the deep eutectic solvent is 2:1 to 1:2.

8. The method according to claim 4, wherein the deep eutectic solvent is prepared from the hydrogen bond donor and the hydrogen bond acceptor in a predetermined stoichiometric ratio by rotary evaporation at 60° C. to 100° C.

9. The method according to claim 4, wherein the amino acid comprises any one of lysine, cystine, and arginine.

10. The method according to claim 4, wherein a molar ratio of the fatty acid to the amino acid is 2.5:1 to 1:1.

11. The method according to claim 1, wherein the gemini lipoamino acid comprises lauric acid.

12. The method according to claim 1, wherein the amino acid is glycine.

13. The method according to claim 11, wherein the amino acid is glycine.

14. The method according to claim 1, wherein the deep eutectic solvent comprises any one of betaine-glycerin or betaine-xylitol.

* * * * *